United States Patent
Hirono et al.

(10) Patent No.: US 6,719,203 B2
(45) Date of Patent: Apr. 13, 2004

(54) CUVETTE CONTROL UNIT AND CONTROLLING METHOD USING THE SAME

(75) Inventors: Taisuke Hirono, Ibaraki-ken (JP); Muneharu Ishikawa, Ibaraki-ken (JP)

(73) Assignee: Kowa Company, Ltd., Aichi-Ken (JP)

( * ) Notice: Subject to any disclaimer, the term of this patent is extended or adjusted under 35 U.S.C. 154(b) by 150 days.

(21) Appl. No.: 09/901,288

(22) Filed: Jul. 9, 2001

(65) Prior Publication Data

US 2002/0009395 A1 Jan. 24, 2002

(30) Foreign Application Priority Data

Jul. 10, 2000 (JP) .......................................... 2000-209021

(51) Int. Cl.$^7$ ................................................. G06K 7/10
(52) U.S. Cl. .............. 235/462.13; 235/385; 235/462.01
(58) Field of Search ........................... 235/385, 462.13, 235/462.01

(56) References Cited

U.S. PATENT DOCUMENTS

| | | | | |
|---|---|---|---|---|
| 4,729,661 A | * | 3/1988 | Bell | 356/436 |
| 4,900,513 A | * | 2/1990 | Barker et al. | 422/64 |
| 5,386,287 A | * | 1/1995 | Berssen et al. | 356/326 |
| 5,391,352 A | * | 2/1995 | Hendrix et al. | 422/65 |
| 6,012,638 A | * | 1/2000 | Ackley et al. | 235/462.01 |
| 6,279,828 B1 | * | 8/2001 | Fann | 235/462.01 |

* cited by examiner

*Primary Examiner*—Michael G. Lee
*Assistant Examiner*—Seung H Lee
(74) *Attorney, Agent, or Firm*—Duane Morris LLP

(57) ABSTRACT

Cuvettes in boxes for blood testing and the like, are to be distinguished by bar code cuvette identification codes on each cuvette, together with a box identification code. The cuvettes have very limited space for bar code characters. The cuvette bar code reader is responsive to at least two different kinds of control codes, i.e., two distinct start code values and/or stop code values. The distinct control codes operate the bar code reader, but also contribute to the information that is encoded. A cuvette identification code is developed that combines an information code value with distinctions among the control codes found, to increase the number of values that can be encoded. In one embodiment, four start codes, four stop codes and a single decimal information digit, provide 160 different values.

7 Claims, 14 Drawing Sheets

| IDENTIFICATION INFORMATION INF (ID IN CUVETTE BOX) | START CODE S | DATA CODE I | STOP CODE P |
|---|---|---|---|
| a 1 a | a | 1 | a |
| a 1 b | a | 1 | b |
| a 1 c | a | 1 | c |
| a 1 d | a | 1 | d |
| a 2 a | a | 2 | a |
| a 2 b | a | 2 | b |
| ... | ... | ... | ... |
| ... | ... | ... | ... |
| ... | ... | ... | ... |
| ... | ... | ... | ... |
| c 8 d | c | 8 | d |

| RECORD No. (CUVETTE ID) | CUVETTE BOX ID | IDENTIFICATION INFORMATION INF (ID IN CUVETTE BOX) | BLOOD PRODUCTS ID | REGISTRATION FLAG | MEASUREMENT FLAG |
|---|---|---|---|---|---|
| 000000000001 | 000000001 | | | 0 | 0 |
| 000000000002 | 000000001 | | | 0 | 0 |
| 000000000003 | 000000001 | | | 0 | 0 |
| 000000000004 | 000000001 | | | 0 | 0 |
| 000000000005 | 000000001 | | | 0 | 0 |
| ... | ... | | | ... | ... |
| ... | ... | | | ... | ... |
| ... | ... | | | ... | ... |
| ... | ... | | | ... | ... |
| 000000000096 | 000000001 | | | 0 | 0 |

(b) TB

| RECORD No. (CUVETTE ID) | CUVETTE BOX ID | IDENTIFICATION INFORMATION INF (ID IN CUVETTE BOX) | BLOOD PRODUCTS ID | REGISTRATION FLAG | MEASUREMENT FLAG |
|---|---|---|---|---|---|
| 000000000001 | 000000001 | a 1 a | 0000000001 | 1 | 0 |
| 000000000002 | 000000001 | a 1 b | 0000000002 | 1 | 0 |
| 000000000003 | 000000001 | a 1 c | 0000000003 | 1 | 0 |
| 000000000004 | 000000001 | a 1 d | 0000000004 | 1 | 0 |
| 000000000005 | 000000001 | a 2 a | 0000000005 | 1 | 0 |
| ... | ... | ... | ... | ... | ... |
| ... | ... | ... | ... | ... | ... |
| ... | ... | ... | ... | ... | ... |
| ... | ... | ... | ... | ... | ... |
| ... | ... | ... | ... | ... | ... |
| 000000000096 | 000000001 | c 8 d | 0000000096 | 1 | 0 |

| IDENTIFICATION INFORMATION INF (ID IN CUVETTE BOX) | START CODE S | DATA CODE I | STOP CODE P |
|---|---|---|---|
| a 1 a | a | 1 | a |
| a 1 b | a | 1 | b |
| a 1 c | a | 1 | c |
| a 1 d | a | 1 | d |
| a 2 a | a | 2 | a |
| a 2 b | a | 2 | b |
| ... | ... | ... | ... |
| ... | ... | ... | ... |
| ... | ... | ... | ... |
| c 8 d | c | 8 | d |

CUVETTE CONTROL UNIT AND CONTROLLING METHOD USING THE SAME

BACKGROUND OF THE INVENTION

This invention relates to a unit for controlling cuvettes used when counting leukocytes in blood products.

When counting the number of leukocytes in blood products, it is known to mix the blood products with a hemolysis fluorescent dyeing reagent. FIG. 1 is a view showing a cuvette, (a) being a side view and (b) being a view seen from arrow A of (a). The cuvette 1 is a container for holding blood products with the reagent therein, during measurement. Cuvette 1 has a hollow main body 2 made of colorless transparent plastic and a colored lid 3 made of rubber, as shown in FIG. 1. The main body 2 is open on top, its opening portion has an installation portion 2d for the lid 3. The lid 3 is attachably and detachably installed on this installation portion 2d. Below the installation portion 2d of the main body 2, a body portion 2c in a cylindrical shape is formed. Below the body portion 2c is a taper portion 2b. At the lower end of the taper portion 2b, a plate portion 2a is provided. The whole main body 2 and the plate portion 2a are formed integrally. The whole has a shape like a cone narrowing downwardly. The lid 3 is inserted into the installation portion 2d, and the installation portion 2d is a cylindrical shape having the diameter bigger than one of the body portion 2c so as not to drop the lid 3 into the body portion 2c.

For counting number of leukocytes in blood products using the above-mentioned cuvettes 1, a number of empty one-use cuvettes 1 (for example 96 cuvettes) are provided in a cuvette box, and are taken individually and identified by marking an ID number on the main body 2 of each of the cuvettes 1 with a marking ink A unique ID number is affixed on blood products bag when blood is collected. The blood products ID and the cuvette ID are each correlated by entries in a note book or the like.

Subsequently, 100 μL of hemolysis™ fluorescent dyeing reagent, for instance, is respectively added to the ninety six (96) cuvettes 1. Thereafter, 100 μL of the blood, for instance, is extracted from the blood products, and the extracted blood is added to the cuvette 1, wherein the reagent and the blood mix and react. The above-mentioned operation is repeated for each of the ninety six cuvettes 1 in order. Thereafter, the cuvette 1 in which the reagent and the blood products are reacted is taken out and centrifuged. Then, the cuvette 1 is taken out of the centrifuge and set on a micro-leukocytometer.

At this point, it is necessary manually to input the blood products identification in the micro-leukocytometer. In this machine, laser beams are exposed to the leukocytes the lower end of the cuvette 1, and the image is analyzed with a CCD camera or the like from the lower end or the side so as to count the number of the leukocytes. The counted result is displayed, correlated with the input blood products identification, and printed or stored in a memory medium.

In a conventional method of controlling cuvettes, it is necessary for a tester to read the identification number from each of the cuvettes 1 and to enter the cuvette ID number against the blood products ID number in a separate list, so as to establish the correspondence between these numbers. But this is a close operation because the cuvette 1 is about 30 mm in total length and has a maximum diameter of about 18 mm, for instance. The cuvette is small. Besides, ninety six (96) cuvette ID number entries must be made to complete one box, and ninety six (96) correlations of cuvette and blood product ID numbers are also necessary. The ID numbers may encode information such as the blood center, the place where the blood was collected, and a serial number, in the blood products ID. This ID is a 10 digit number. As mentioned before, the blood products ID is manually input at a measuring instrument. There are problems in such an operation, for instance, there is a possibility of error. In any event, the tester is subject to strong mental stress and physical pain.

For these reasons, each cuvette 1 might be controlled using bar codes of the sort used for individual data control in other fields. But, the cuvette 1 is small. For this reason, the area where a bar code might be affixed is small. There are problems if one attempts to affix and use conventional bar code.

An object of the present invention is to provide a cuvette control unit capable of controlling cuvettes 1 by using bar code even though the cuvette is small and the area for affixing a bar code is limited.

SUMMARY OF THE INVENTION

According to an inventive aspect, a cuvette control unit is provided for controlling cuvettes by reading a first bar code affixed on said cuvette, said first bar code being comprised of control code characters located on opposite end portions, and information codes located between said control codes. The cuvette control unit comprises: a first reading means capable of reading said first bar code; a cuvette identification information producing means for producing cuvette identification information corresponding to said cuvette on which said first bar code is affixed from said control code characters and said information codes of said first bar code read by said first reading means; and a memory means for storing said cuvette identification information produced by said cuvette identification information producing means, corresponding to said cuvette on which said first bar code is affixed.

According to an inventive aspect, the capacity of the identification information on the cuvette is increased because a number of different kinds of control codes are used and can distinguish between identification codes that otherwise have the same digits of information code between said control codes. Therefore, sufficient capacity of the identification information is obtained for identifying the cuvettes. In fact, the information capacity encoded by a given number of code digits is increased (or the necessary number of digits to encode the same information is decreased) as compared to the number of digits of information code and/or information capacity of a general bar code of comparable size and/or capacity. That is, identification and control of cuvettes are possible with smaller bar code, having fewer digits, than a general bar code.

According to one application of this aspect, the control codes used in said first bar code comprises a start code that has at least two distinct kinds. Identification information is encoded by the kind of start code used in the control code. When this control code distinction is used in the first bat code together with information code, the information capacity of the first bar code is increased according to the number of kinds of the start code. More cuvettes can be identified and controlled than in a general bar code having the same number of digits.

Alternatively or in addition, said first bar code can have two or more distinct kinds of stop code used in the control codes. As described above with respect to having distinct start codes as control codes, the capacity of the identification information of the bar code can be increased according to the number of distinct kinds of the stop code. Given the same number of digits of information code plus these distinct kinds of control codes, can be identified and controlled.

In one embodiment, the cuvette control unit and cuvette identification information producing means uses identification information for said cuvette, namely said first bar code affixed thereto, with start code as one control code and a stop code as another control code. Part of the identification information is produced from the control codes, particularly a start code and a stop code. The number of distinct identification values possible with bar code containing multiple kinds of start codes and multiple kinds of stop codes, wherein the number of digits of information code between the control codes is the same, is increased according to the number of kinds of the start code and the stop code For instance, ninety six (96) cuvettes, which are generally used, can be identified and controlled even with one digit of information code.

The increased formation capacity provided in this way can be used for additional purposes. For example, said first bar code can be comprised of control codes comprising multiple kinds of start code and stop code, one digit of identifying information code and one digit of inspection code.

In this embodiment, cuvettes can be identified and controlled with four digits or characters. The cuvette identification information can be obtained by the first bar code comprised of control codes comprised of the start code and the stop code, one digit of code for information, plus said digit of inspection code. Althoughthe bar code may be affixed to a cuvette and the area for the bar code label is limited, so the cuvettes can be identified and controlled.

The invention accommodates the fact that a plurality of said cuvettes are stored in a cuvette box. A second bar code is affixed on the box. A second reading means is capable of reading said second bar code. A cuvette box identification information producing means produces box identification information corresponding to the cuvette box carrying the second bar code. A storing control means for stores said cuvette identification information corresponding to the individual cuvettes, and said cuvette box on which said second bar code is affixed. The corresponding information is stored in said memory means is provided.

The cuvette box identification codes and the cuvette identification information are correlated when stored in the memory means. Thus, the identification information can be further increased. The number of different possible code combinations capable of identifying and distinguishing one cuvette from another is further increased. The identification of cuvettes can be perfected.

The invention can further support encoding, storing and relating further coded information identifying the blood products. Information obtained from a third bar code affixed on a blood products storing means can be used together with the cuvette encoding techniques and memory means as described, when processing and controlling blood products using said cuvettes.

BRIEF DESCRIPTION OF THE DRAWINGS

FIG. 5 is a view for showing an identification (ID) correlation table list, for registering cuvette IDs and the like;

FIG. 14 shows an example when the contents of a code corresponding to the identification information INF of an ID in a cuvette box are entered with start code S, data code I and stop code P.

DESCRIPTION OF THE PREFERRED EMBODIMENTS

Figure 1:
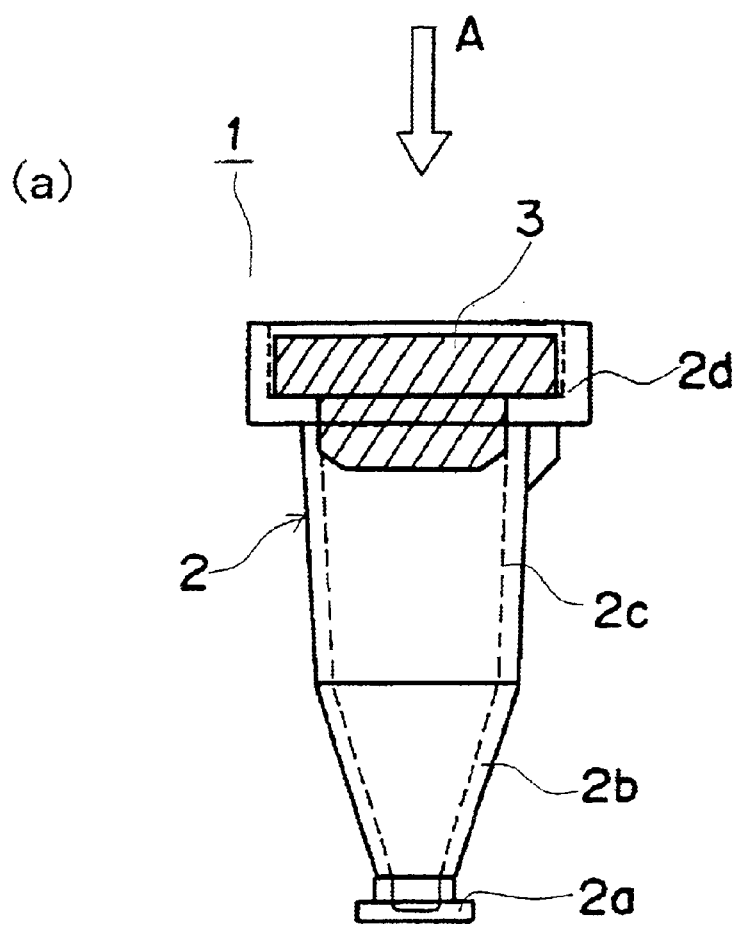
FIG. 1 shows a cuvette according to the present invention, (a) being a side view, and (b) a view seen from arrow A of (a)
Figure 1:
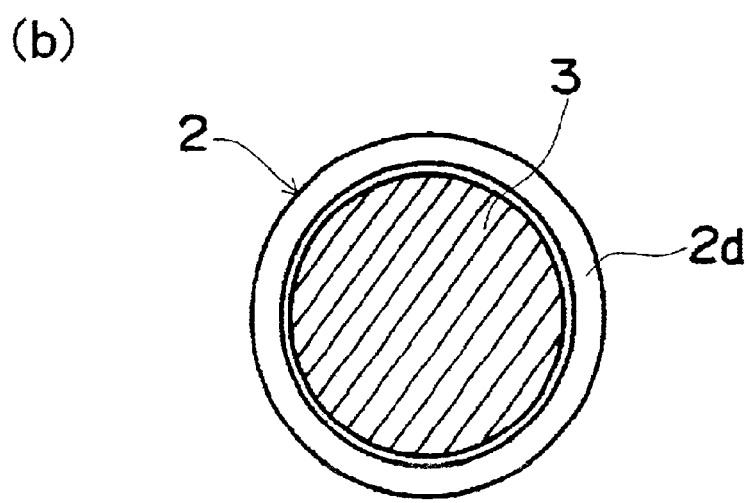

Embodiments of the present invention will now be explained, referring to the drawings.

The invention is applicable to a conventional cuvette 1, as described above in the "BACKGROUND OF THE INVENTION". So, its explanation is not repeated here (see FIG. 1). FIG. 2(a) is a view for showing an exemplary position of a first bar code 5 ("bar code label" hereinafter) affixed on the cuvette 1. The bar code label 5 is affixed so as to wind around an outer periphery of the installation portion 2d of the lid, which has the maximum diameter found on the cuvette main body 2.

Figure 10:
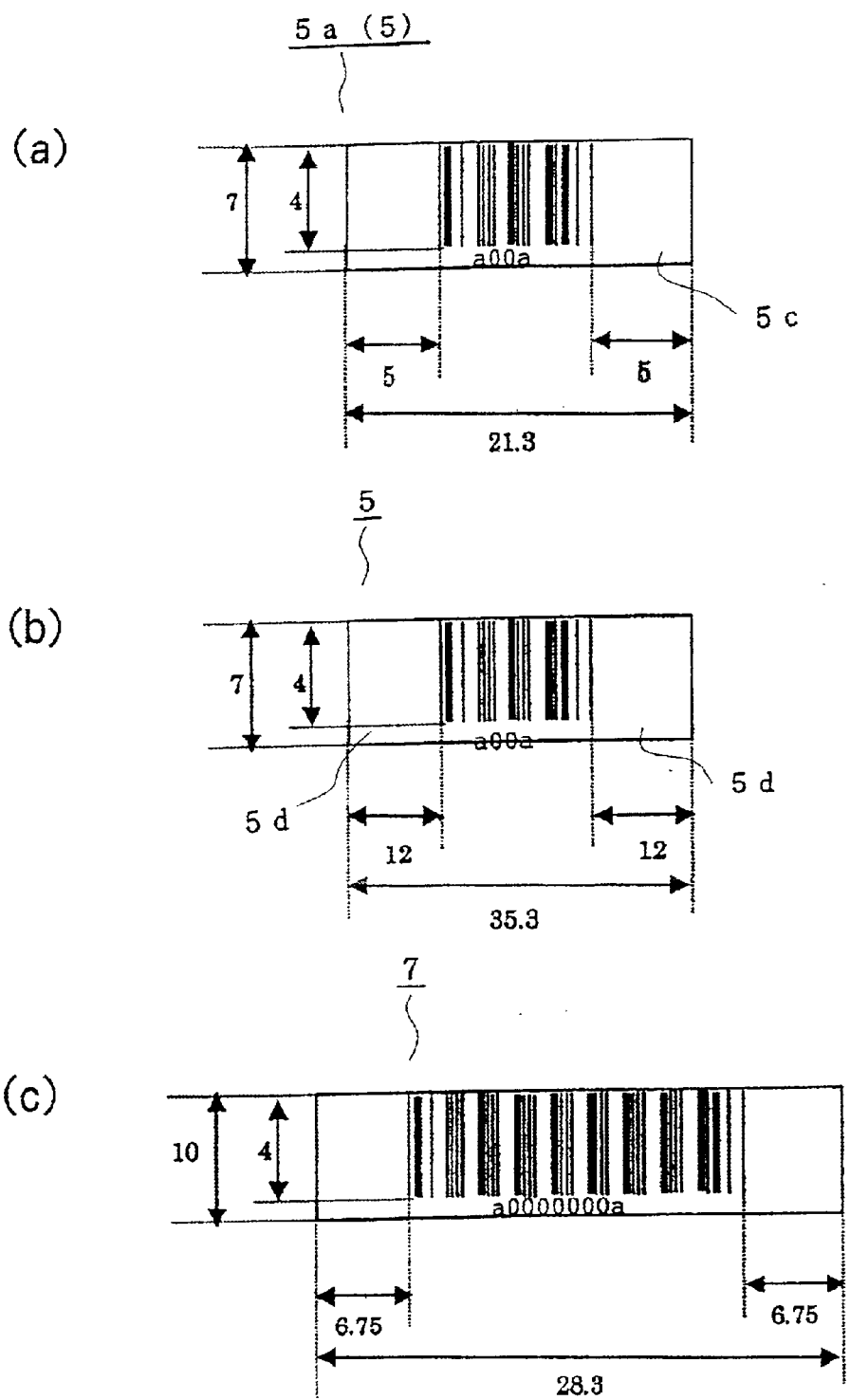
FIG. 10 shows an example of the bar code label, (a) being a general bar code label ID for a cuvette box, (b) a bar code label of an ID for a cuvette box of the present embodiment and (c) is a bar code label cuvette box ID.

FIGS. 10(a) and (b) each shows an example of the bar code label 5. (The numeric value in the figure shows dimensions in mm). The area for affixing the bar code label 5 on the cuvette 1 is limited, because the cuvette 1 is small in size.

Figure 2:
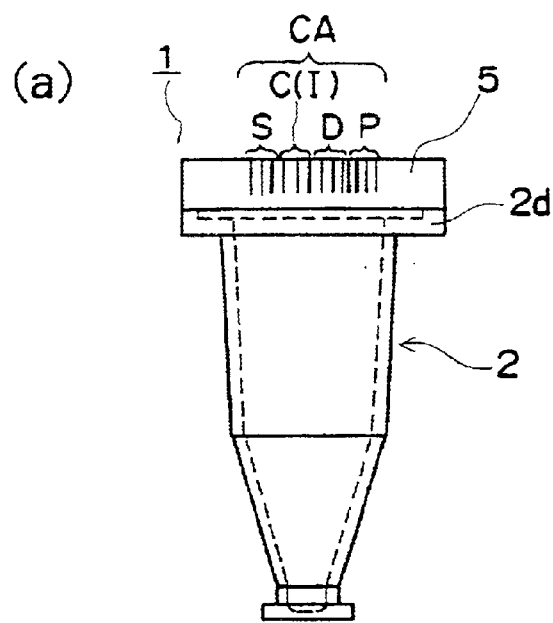
FIG. 2 is a view showing an example of positions at which a bar code label can be affixed according to the present invention, (a) showing the bar code label of a cuvette, (b) the bar code label of cuvette box, and (c) the bar code label of blood products bag.
Figure 2:
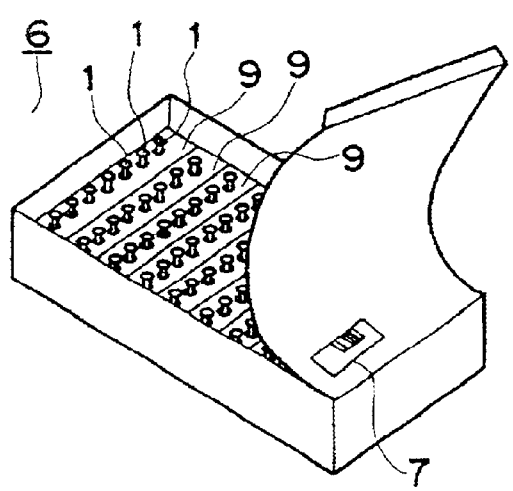
Figure 2:
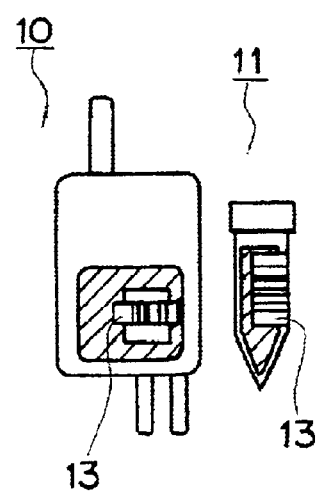

The bar code label 5 is affixed on the outer periphery portion of the installation portion 2d of the upper lid, at the surface having the maximum diameter, because the contents of the bar code can not be seen if the label 5 is affixed on the body portion 2c of the cuvette 1 (see FIGS. 1 and 2). It is inevitable that the label must be small, to carry a bar code, such as bar code label 5a as shown in FIG. 10(a).

Figure 12:
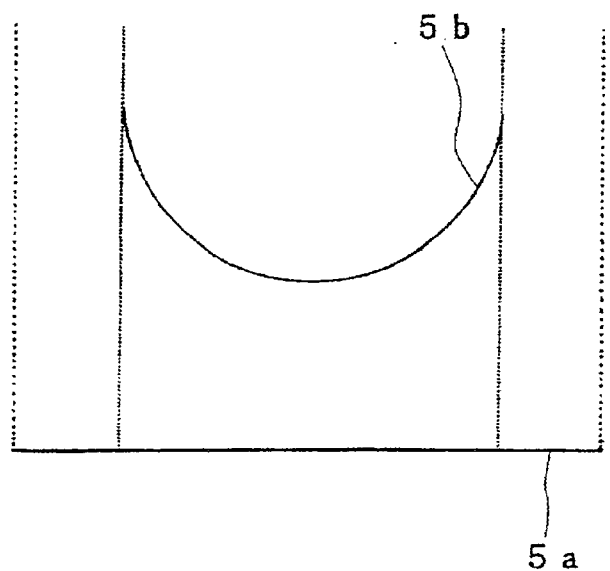
FIG. 12 is a view for comparing the bar code label in straightened state and the bar code label in the state of being affixed on the cuvette, (a) being a top view and (b) a view seen from arrow B of (a)
Figure 12:
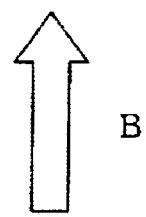
Figure 12:
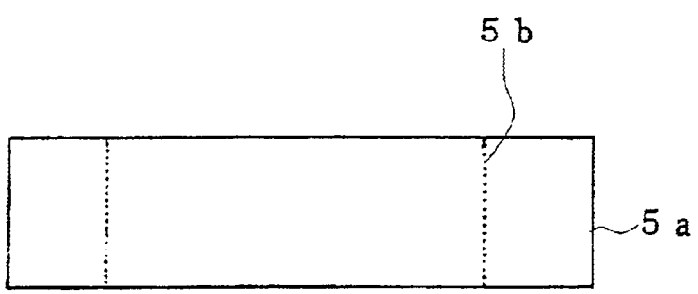

FIG. 12 is a view showing the difference between the bar code label in a straightened state and the bar code label affixed on the cuvette, (a) being aplan view and (b) being a view seen from arrow B in (a). The installation portion 2d of the lid of the cuvette 1 is a circular shape seen in plan view, as shown in FIG. 1(b). If a general bar code label 5a as shown in FIG. 10(a) is affixed on the installation portion 2d of the lid and a bar code label 5b affixed on the circular shape is projected and seen in elevation from the side, in the direction as shown by the arrow A, the label is foreshortened on the right and left sides as shown in FIG. 12 in comparison with the straight bar code label 5a. For this reason, the effective code reading breadth with respect to margin portions 5c at the right and left of the bar code label 5a, is decreased. This makes it difficult to read the bar code label 5a using a bar code reader 14.

As shown in FIG. 10(b), margin portions 5d of 12 mm are provided on the exemplary bar code label 5. The label can have a span greater than half of the circumference of the installation portion 2d of the lid (in elevation view the part of the view occupied by the label is relatively larger than when considering the curved circumference) by generally making the margin portion 5c longer than 5 mm. A longer bar code label 5a may be more easily read with the bar code reader 14, except for the matter of the curve.

FIG. 2(b) is a view for showing an example of a position of a second bar code ("bar code label" hereinafter) 7 which is affixed on a cuvette box 6, and FIG. 10(c) is a view for showing an example of the bar code label 7. The cuvette box 6 can be made with corrugated cardboard or the like, and carries twelve (12) rows of cuvette stands 9. On each cuvette stand 9, eight (8) cuvettes 1 are arranged in a row. There are thus twelve (12) rows×eight (8) cuvettes per row=ninety six (96) cuvettes 1 in the cuvette box 6. The bar code label 7 is affixed on the outside upper portion or otherwise on the outer periphery of the cuvette box 6.

FIG. 2(c) shows an exemplary third bar code ("bar code label" hereinafter) 13 affixed on a blood products bag 10 (bag shape) or 11 (bottle shape). The bar code label 13 is affixed on the surface of the blood products bag 10 or 11.

Figure 3:
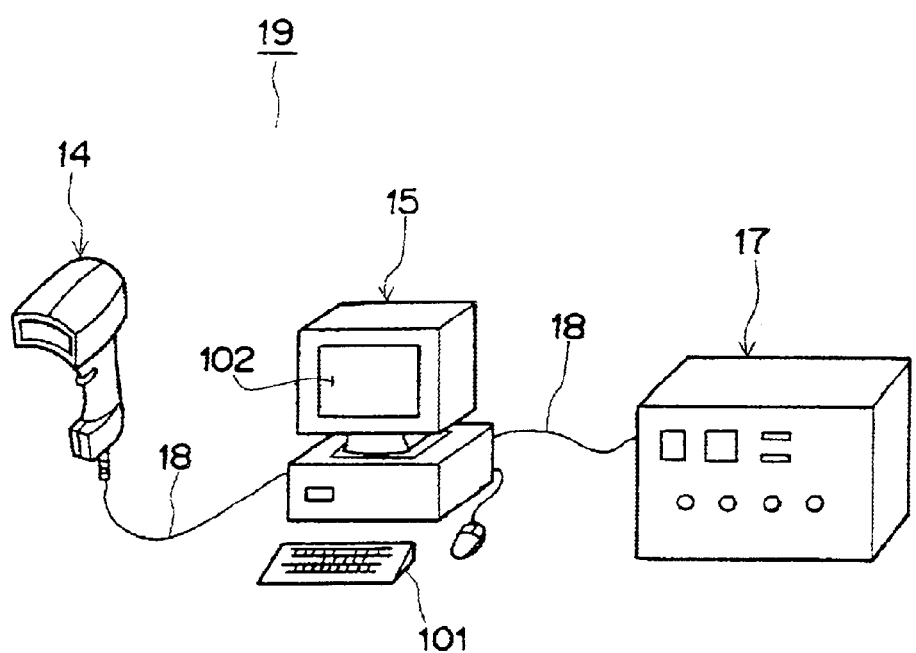
FIG. 3 is a view showing an example of a cuvette control unit according to the present invention.

FIG. 3 shows an example of a cuvette control unit 19. The cuvette control unit 19 has reading means ("bar code reader" hereinafter) 14, which is a known electronic device, a micro-leukocytometer 17 and a computer 15, as shown in FIG. 3. The bar code reader 14 and the micro-leukocytometer 17 are connected with the computer 15 via connection cables 18, 18. In this example, the first reading means and the second reading means use the same bar code reader, but a plurality of bar code readers may be used instead.

Figure 13:
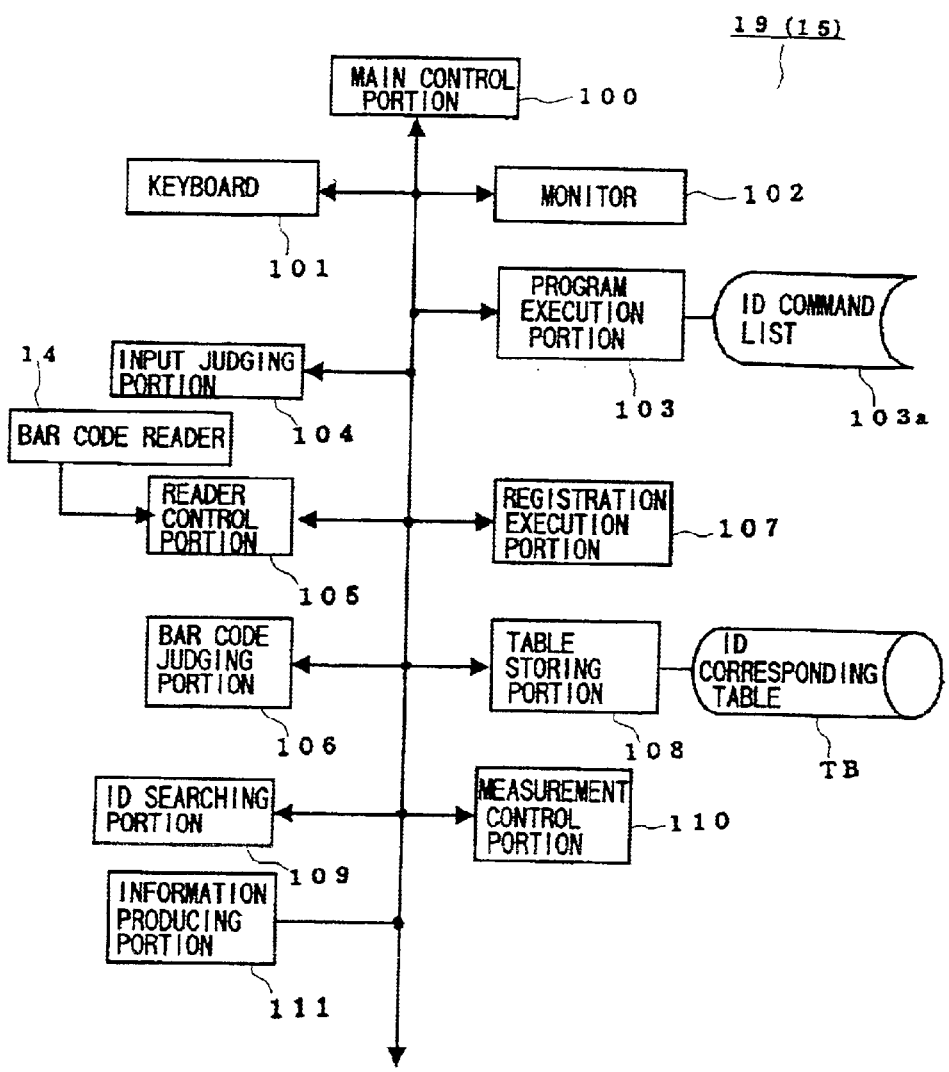
FIG. 13 is a block diagram showing an example of a structure of the cuvette control unit according to the invention.

FIG. 13 is a block diagram showing an exemplary computer system for the cuvette control unit. As shown in FIG. 13, a main control portion 100 is provided with the computer 15. With the main control portion 100, a keyboard 101, a monitor 102, a program execution portion 103, an input judging portion 104, a reader control portion 105, a bar code judging portion 106, a registration execution portion 107, a table storing portion 108, an ID searching portion 109, a measurement control portion 110, and an information producing portion 111 are provided. An ID command list 103a is held by the program execution portion 103. Besides, an ID corresponding table (ID corresponding list) TB is stored in the table storing portion 108, and the bar code reader 14 is connected with the reader control portion 105, which is arranged to control the bar code reader.

Figure 4:
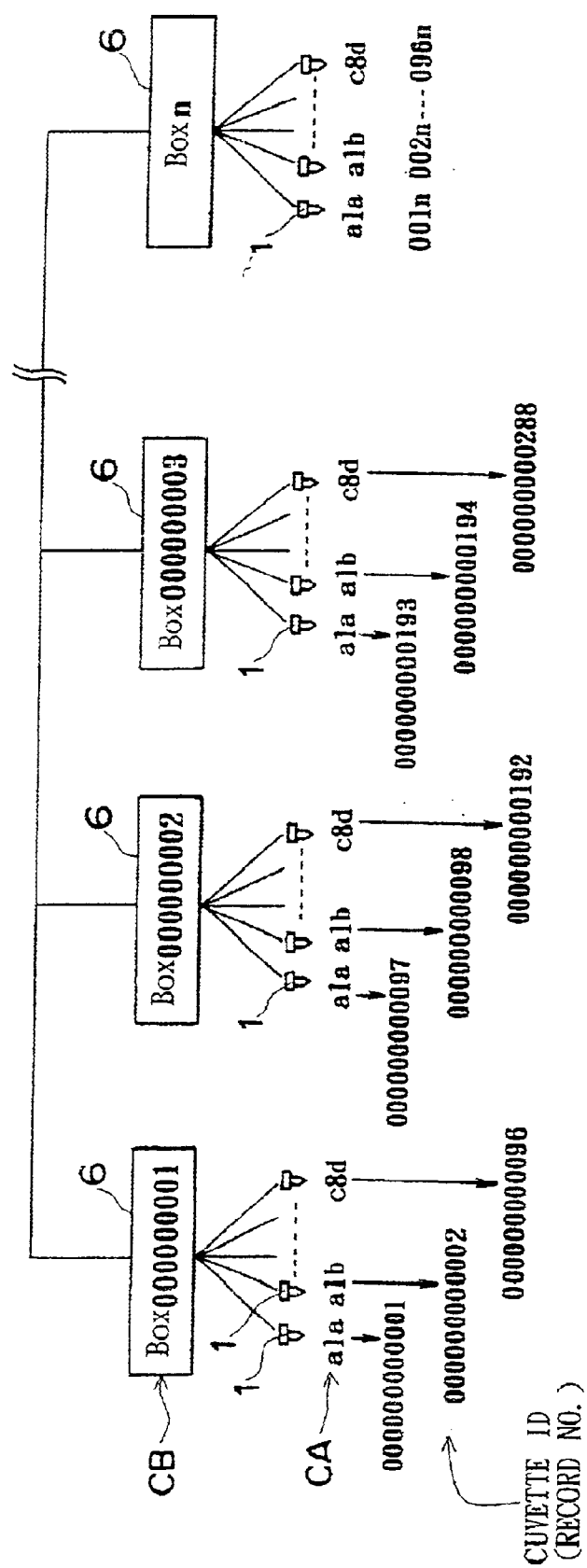
FIG. 4 shows a conceptual a structure for using bar code.

FIG. 4 is a conceptual view for showing an example of how the bar code is used. As mentioned before, the bar code label 7 is affixed on the cuvette box 6, and the bar code label 5 is affixed to the cuvette 1. A bar code CA capable of encoding at least ninety six (96) distinct values (i.e., the number of the cuvettes 1 from one cuvette box 6 that are to be distinguished from one another) appears on the bar code label 5 to be affixed on each cuvette 1. This value of the bar code CA identifying each cuvette 1 in each cuvette box 6, is the value, for example, "a1a", "a1b", . . . "c8d", shown in FIG. 4. Bar code CB is capable of encoding n (or more) values (where "n" is the total number of cuvette boxes 6 to be distinguished from one another using the bar code label 7 affixed on the cuvette box 6. The value of bar code CB for identifying each cuvette box, is the "cuvette box ID", and is the value, such as "000000001", "000000002", "000000003" . . . "n", for instance, as shown in FIG. 4. Similarly, the bar code CA is the "cuvette ID." That is, ninety six (96) (the number of encoded cuvettes in each box)×n (the total number of distinguishable boxes) defined the number of cuvettes can be indentified and distinguished by the bar codes CA and CB used together with each other in a hierarchy as shown in FIG. 4. Thus, a unique cuvette data ID is provided by the combined cuvette ID (the bar code CA) and cuvette box ID (the bar code CB). The combined ID distinguishes 96×n cuvettes 1 (the CUVETTE ID) each corresponding to a record number in the table mentioned hereinafter). The value of the bar code shown on the bar code 13 of the blood products bag 10, 11 is its blood products information ("products ID" hereinafter).

Figure 6:
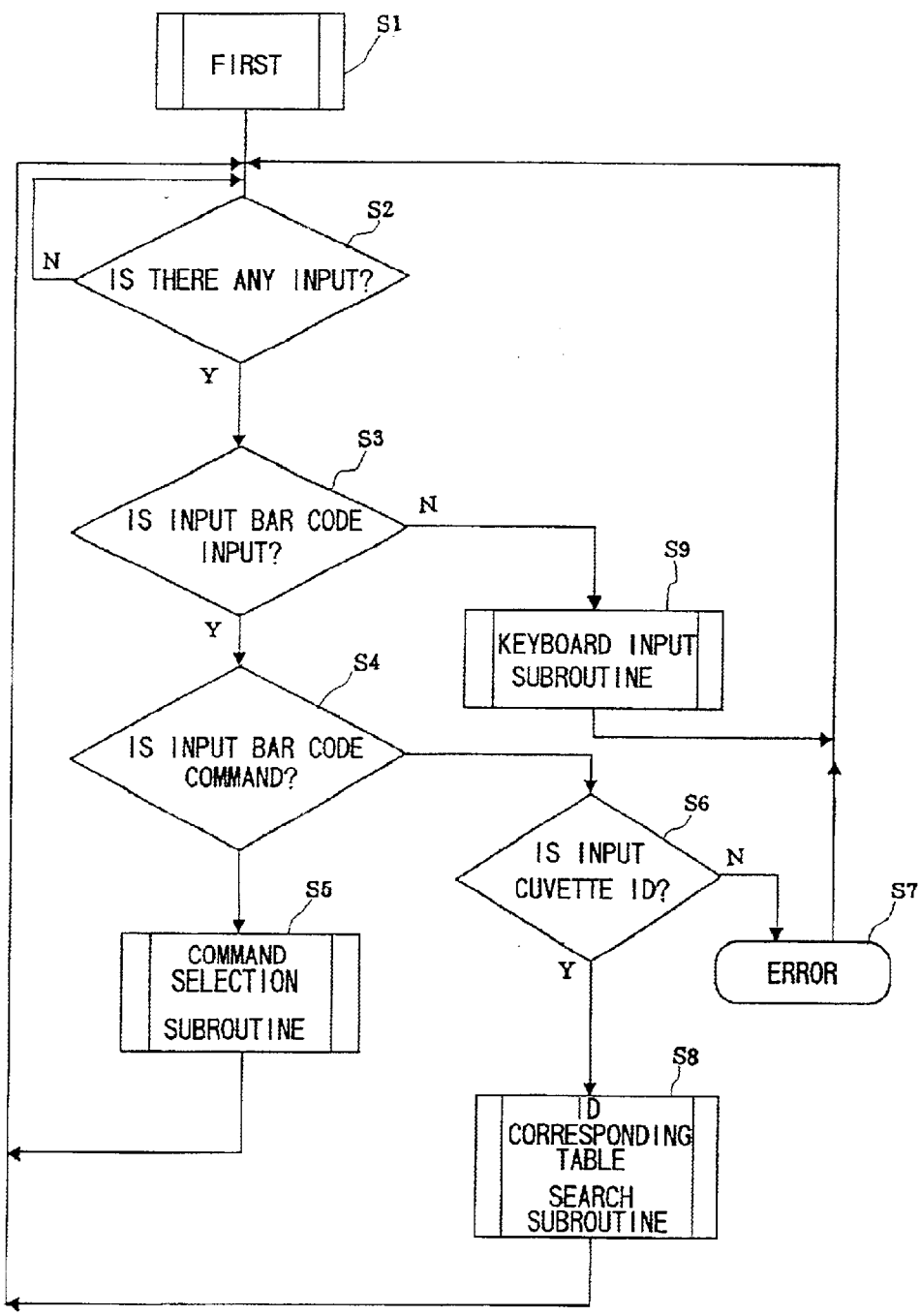
FIG. 6 is a flowchart showing an exemplary process control program set in a computer.

As thus arranged, an operation is executed as follows. FIG. 6 is a flowchart for showing an example of the process steps of the control program, set in the programming of computer 15.

A tester inputs a start command to commence the control program through the keyboard 101 of the computer 15 or the like. The start command is transfers execution to the main control portion 100. The main control portion 100 instructs the program execution portion 103 to execute the control program and commences the control program (see FIG. 13). At startup, a predetermined initial process routine, such as the initialization of parameter values (shown with "FIRST" in FIG. 6) is executed (step S1).

As a first step, a cuvette ID is registered. A tester causes the bar code reader 14 to read a predetermined bar code (not shown) (such as a bar code for a registration command). The code information is input by the reader control portion 105. The input judging portion 104 determines whether or not there is any input of information (step S2). When there is an input of information, the information is judged to determine whether or not it is a valid bar code input (step S3). In the case that the information is a valid bar code input, the program enters step S4 via step S2 and step S3. See FIG. 6.

The bar code judging portion 106 determines whether or not the information input at the bar code input is a bar code command (step S4). As mentioned before, a predetermined bar code value (e.g., bar code command or bar code data) was read by the bar code reader 14. The bar code judging portion 106 judges whether this is the bar code command. Upon receiving a determination that the data is a bar code command, the program execution portion 103 executes command selection sub-routine (step S5).

Figure 8:
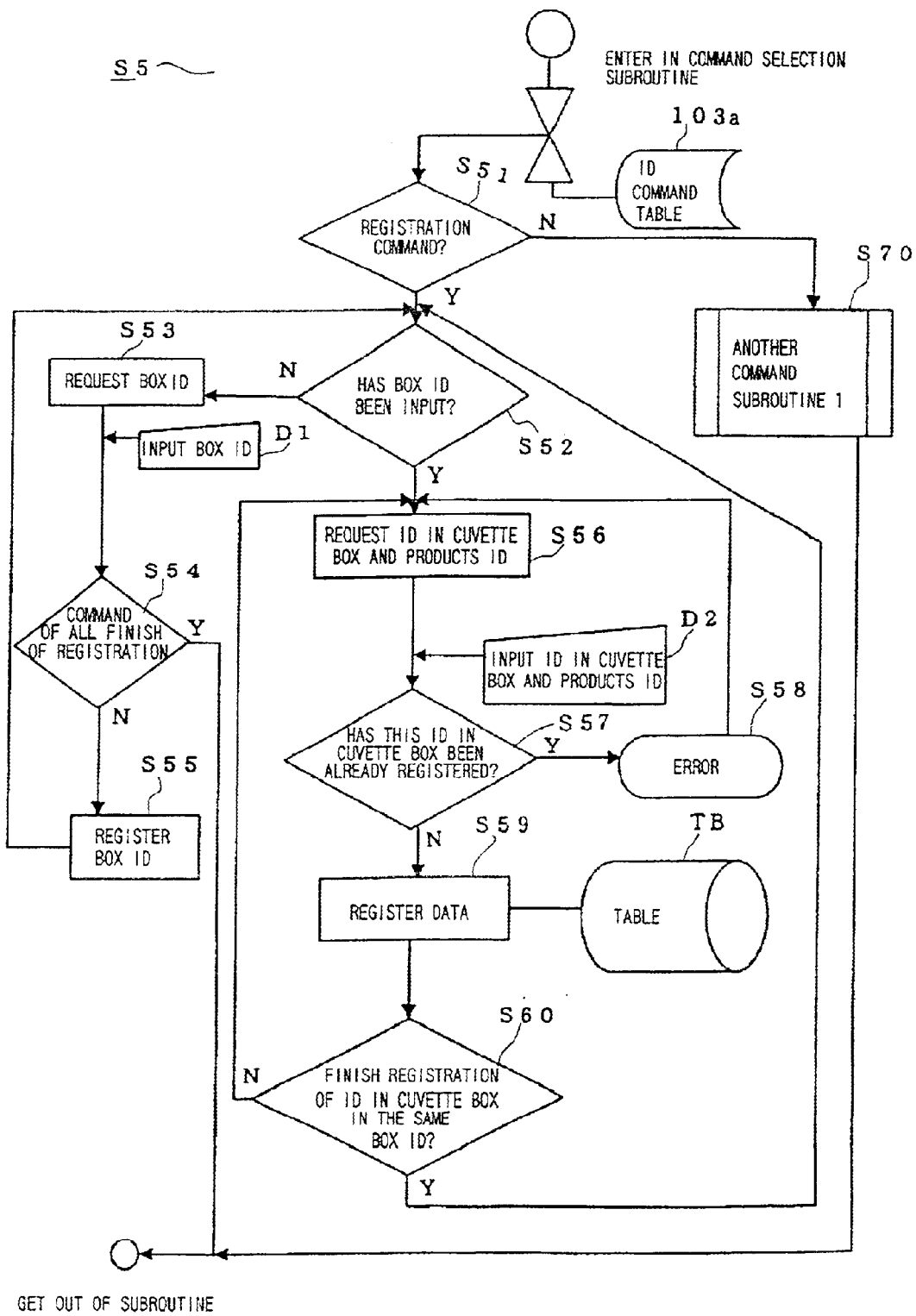
FIG. 8 is a flowchart showing an exemplary command selection subroutine.

FIG. 8 is a flowchart for showing an example of command selection sub-routine. The bar code judging portion 106 determines whether or not the information found is registered as a command, and interprets the information by referring to an ID command list 103a stored in the program execution portion 103 beforehand (step S51). In the case that the information isregistered, the program proceeds with the following step S52.

FIG. 5 is a view showing an ID correspondence table for registering a cuvette ID or the like. The registration execution portion 107 calls the table TB as shown in FIG. 5(a), stored in the table storing portion 108, and judges the possibility of inputting a record to the table TB. In the present embodiment, an input pointer (not shown) is produced to identifying a position in the table TB, from the value of the cuvette box ID. A judgment as to whether or not the above-mentioned record can be input is done similarly for a cuvette ID of a cuvette box ID (step S52).

When a judgment is made that a cuvette box ID has not been input but is needed to start registration, the registration execution portion 107 outputs a request for inputting a cuvette box ID (step S53). This request is executed by displaying a message through the monitor 102, for instance. Responding to this request, the tester causes the bar code reader 14 to read the bar code label 7 of the cuvette box 6. When all the registrations are finished, a command for registration finish is read and input instead of a bar code label 7 of a cuvette box 6. The program enters step S55 if the command for registration finish is not input at step S54.

The information that was read is input through the reader control portion 105, and appropriately stored in a predetermined field of the table TB of the table storing portion 108 by the registration execution portion 107, namely as a cuvette box ID (step S55). In FIG. 5(a), for instance, the cuvette box ID which is "000000001" is the datum stored for "cuvette box ID" in the table TB.

When the cuvette box ID is thus input, the program enters step S52 again, as shown in FIG. 8. The cuvette box ID steps having been done, registration execution portion 107 requests input to correlate the cuvette box ID with a products ID (step S56). This request is done by displaying message through the monitor 102, for instance. Meanwhile, hemolysis™ fluorescent dyeing reagent has been injected into each cuvette 1. Furthermore, blood extracted from the blood products is injected into each cuvette 1 so as to mix.

The tester causes the bar code reader 14 to read the bar code label 5 of cuvette 1, and to read the bar code label 13 of a blood products bags 10, 11, namely the bag from which the blood products are taken to be mixed in the cuvette 1. The information that is read is input through the reader control portion 105. Of the bar code input, the bar code CA of the bar code label 5 of the cuvette 1 is input in the information producing portion 111.

Operation of the information producing portion 111 will now be explained.

Figure 11:
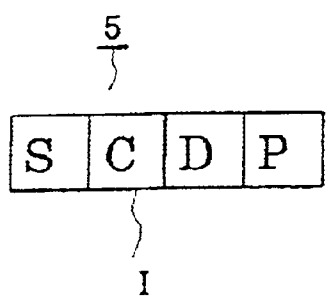
FIG. 11 is a view for showing an example of a structure of the bar code, (a) being a code of ID in a cuvette box and (b) a code of a cuvette box ID.
Figure 11:
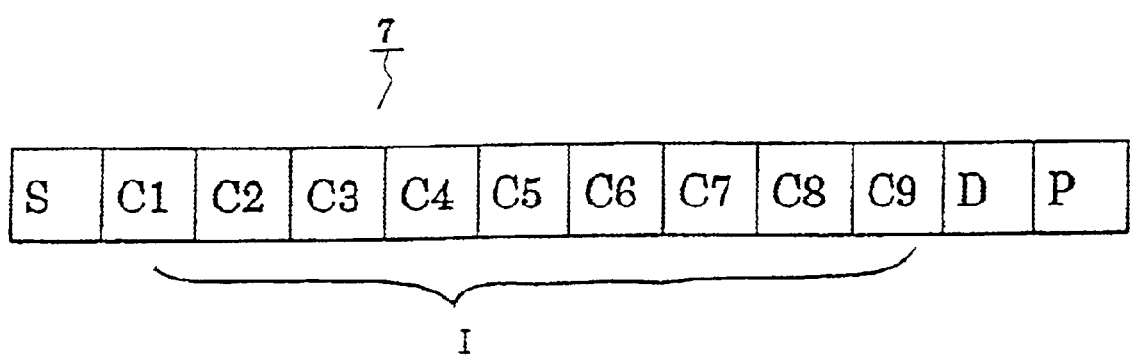

FIG. 11 shows an example of a structure for the code of the bar code label 5 or 7. The character S in the figure is a start code (one of four signals a, b, c, d); C and C1 through C9 represent a data code (e.g., 0 through 9); D is a check digit (a value determined by calculation); P is a stop code (one of four signals, a, b, c, d); and, and the part shown by I is a data code, or flag for information contents. Ninety six (96) distinct codes are provided on the different bar code labels 5 to be affixed respectively to the cuvettes 1, because there are ninety six (96) cuvettes 1 in one cuvette box 6, to be distinguished by their cuvette IDs.

Three categories of digits are provided, in addition to content codes such as numbers, namely the start code S, the check digit D and the stop code P. These start/stop/check categories are generally necessary for bar code, in addition to the data code I representing information content. Since an encoding capacity of ninety six (96) distinct codes (or more) is necessary for the data content code, 2 decimal digits (characters) with decimal numbers zeros to nine are necessary, at the minimum, for 100 distinct values. Then, the bar code has five (5) digits of code if the bar code label 5 is produced as usual. But, in that case the bar code has five (5) digits (characters) of code. It may not be possible to use so large a label, because the space for affixing the bar code label 5 on each cuvette 1 is small. According to the invention, a bar code label 5 having a total of four (4) digits (characters) of bar code is provided, with only one (1) digit of data content code. Nevertheless, sufficient encoding capacity of cuvette identification information is made available for identifying ninety six (96) distinct cuvettes 1, from a total of only four digits of bar code. This is as follows.

FIG. 14 shows usage example when the code corresponding to the cuvette identification information INF (the cuvette IDs of cuvettes in one cuvette box) consists of a start code S, a data code I, and a stop code P. If the start code or leading digit of a line of bar code from a label 5 on the cuvette 1 is read by the bar code reader 14 as an "a," the start code has a data value, e.g., "1." If the stop code is "a," for instance, as shown in FIG. 14, the information producing portion interprets the start code "a" and the stop code "a" as part of the data code in addition to the data code "1," so as to produce the identification information "a1a" from the three (3) digit code. If the start code of the bar code of the cuvette 1 subsequently read is "a," the data code is "1" and the stop code is "b," the information producing portion produces "a1b," and so forth. The cuvette identification information INF comprised of three (3) digits (characters) of data code is produced from four (4) digits (characters) of bar code shown on the bar code label 5 concerning ninety six (96) of cuvettes 1, with start codes and stop codes contributing to the data code as described. The cuvette identification information INF concerning each cuvette 1 is thus produced as shown in FIG. 14.

The start/stop codes can be detected although optional digit (character) values of "a" through "d" are used for start code S and stop code P. That is, four kinds of start code "a" through "d" and four kinds of stop code "a" through "d" are also used as part of the data code. In this way, the capacity of one decimal digit can be increased up to 4×10×4=160 distinct values, using four digits (characters) of bar code and wherein the numeric data code I has one digit (character). In the disclosed embodiment, a capacity of more than 96 variations is more than what is necessary. The he capacity could be made 4×8×4=128 kinds using the numerals "1" through "8" for data code I).

As described, without loss of encoding capacity, the bar code label 5 can be changed from five digits (characters) to to four by providing information wherein the start code and stop code also function partly as data code. Thus, the bar code label size is reduced by a digit. Cuvettes 1 capable of being encoded by bar code are facilitated. The bar code label can be affixed to a limited area, such as the limited area available on the cuvette 1.

As shown in FIG. 11(b), the bar code label 7 of the cuvette box ID can be used in the known way, because the label size is not unduly limited by the size of the box. Twelve (12) digits of bar code label can be used, in which nine (9) digits are data content code. This provides the code of bar code label 7 with a capacity of ($10^9$ distinct possible values to be used for cuvette box identification information).

In that embodiment, the capacity of the cuvette ID together with the box ID is $128 \times 10^9$ in total. The same number of cuvettes 1 can be distinguished using the cuvette control unit 19 as described. As mentioned above, the capacity of the bar code CA of the cuvette ID is easily moved up to 160 (one hundred and sixty) values by producing the cuvette identification information INF. There is no specific limit on the cuvette box identification information INF which is the capacity of the bar code CB on the cuvette box. By providing more than the minimum number of possible data encoding values, the number of cuvettes to be processed at one time can be increased later.

The information producing portion 111 produces the cuvette identification information INF from the start code S, the stop code P and the information code I of the bar code CA (the bar code CA input by the bar code reader 14 is input in the information producing portion 111 so as to produce the cuvette identification information INF. This information is input in the registration execution portion 107. The registration execution portion 107 refers to the table TB in the table storing portion. 108 (to the record also corresponding to the cuvette box ID, which input was judged at step S52 just before). The registration execution portion determines whether or not the cuvette box ID or the cuvette ID just input has been already registered (step S57). If already registered, error processing is performed because a second registration to the same ID is being attempted. An error message or the like is displayed through the monitor 102 or the like. If no registration is judged in step S57, the registration execution portion 107 stores the cuvette ID with the box ID and the blood product ID in respectively predetermined fields in the records, indexing with the input pointer produced for referencing data in table TB (step S59). At the same time, registration flag is set to "1," which indicates "already registered." (Not yet registered is indicated by "0".) In FIG. 5(b), for instance, in the first record of table TB, the cuvette identification information INF (cuvette ID in cuvette box storage area)"a1a" is stored in the item for "cuvette ID in cuvette box." The products ID "0000000001" is stored in the corresponding item of "products ID." A flag is set to "1" in the item of "registration flag."

The values have been thus registered in the fields of cuvette box ID, cuvette ID in cuvette box, and products ID, are associated as one record. As shown in FIG. 5(b), the key item for identifying respective records, which is also the record number, is the cuvette ID. That is, registration of one cuvette ID finishes.

Subsequently, the registration execution portion 107 determines whether or not the registration of cuvette IDs in cuvette box 6 has been finished on the basis of input by the bar code reader 14 or the keyboard 101 (step S60). If not finished, the program returns to step S56, again. By repeating above-mentioned steps S56 through S60 in order, the cuvettes 1 of the particular cuvette box 6 are registered in order. When the program returns to step S56 from step S60, the input pointer in table TB is indexed to the next record in line (see FIG. 5). The same cuvette box ID value is copied from the previous line and correlated with the new cuvette ID value.

When registration is completed for the ninety six (96) cuvettes 1 in the give cuvette box 6, and the program proceeds with step S60, registration of cuvette IDs for the cuvette box is considered finished. This is determined from the input by the bar code reader 14 or the keyboard 101. The program returns to step S52, again, to the next cuvette box. All n cuvette boxes 6 are registered by repeating the above-mentioned steps S52 through S60 in order.

When n×96cuvette IDs are finished, no further registrations are needed. A command indicating that the registration phase has finished is read and/or input, instead of reading the bar code from another cuvette box 6 (operation input D1). The program exists the subroutine for command selection. With step S6 thus finished, the program returns to step S2.

The registered cuvettes (n×96) are centrifuged, and the measurement of the cuvettes 1 is executed via the micro-leukocytometer 17 in the following way.

A tester causes the bar code reader 14 to read the bar code label 7 of a cuvette box 6 and the bar code label 5 of a cuvette 1 of the cuvette box 6.

The input judging portion 104 judges that information is input (step S2), as shown in FIG. 6. Furthermore, input portion 104 judges that the information is bar code input (step S3). The bar code judging portion 106 judges that the information input by bar code input is not a bar code command (step S4), and that the information is a cuvette ID (meaning the combination of a cuvette box ID and a cuvette ID in the cuvette box) (step S6). The program proceeds with step S8 to search the ID correspondence table. If the cuvette ID is not found in step S6, error processing is performed (step S7), and the program returns to step S2.

Figure 7:
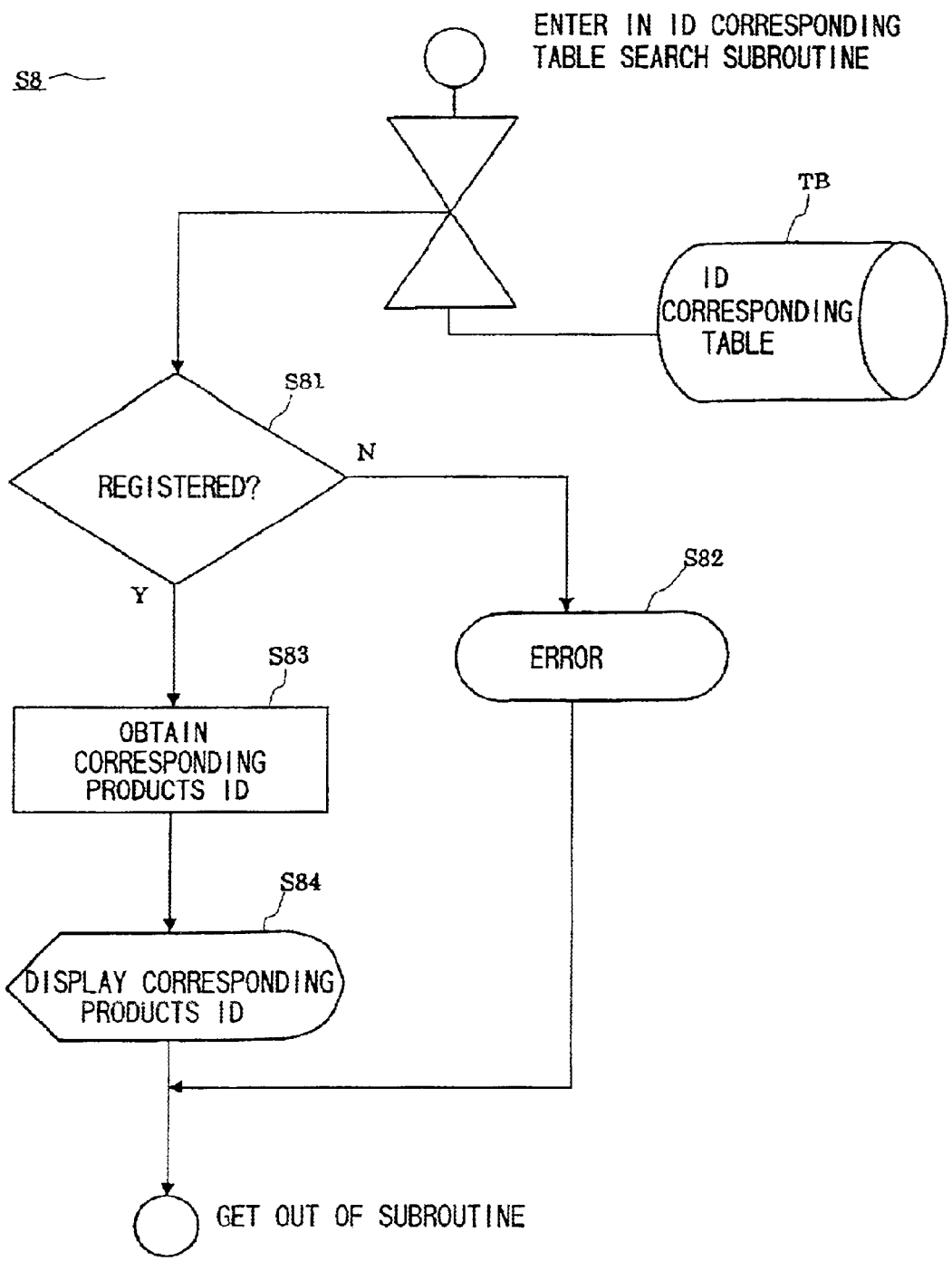
FIG. 7 is a flowchart showing an exemplary of subroutine for searching an ID correlation table.

FIG. 7 is a flowchart for showing an example of the process of searching the ID correspondence table. When the program enters into the subroutine for searching the ID correspondence table of step S8, the main control portion 100 instructs the ID searching portion 109 to search for the subject cuvette and box ID. The ID searching portion 109 searches table TB, in which the cuvette ID (the combination of cuvette box ID and ID in cuvette box) is stored. The subroutine in step S6 judges whether the record having the corresponding cuvette ID exists, that is, whether or not the cuvette ID has been registered (step S81). If the record is not found, error processing is performed (step S82), and the program exists the subroutine to return to step S2, shown in FIG. 6.

When the record having the corresponding cuvette ID is found by searching the table TB in step S81, and the cuvette ID has been registered, the correspondence table TB also can be consulted to obtain the corresponding products ID included in the record searched (step S83). The products ID thus bound is displayed on the monitor 102 or the like (step S84). Watching this display, an operator confirms the products ID. At the same time, the products ID obtained in step S83 is directly transferred to the micro-leukocytometer 17 through the connection cable 18.

When the products ID is sent as an input to the micro-leukocytometer 17, the program exists the subroutine for searching the ID corresponding table and returns to Step S2, shown in FIG. 6.

It is possible to provide the products ID by manual input through the keyboard 101, rather than scanning a code. When the products ID is manually input through the key board 101 or the like, for instance, the input judging portion 104 determines that the information has been input (step S2), that the information is not bar code input (step S3), as shown in FIG. 6. In that case, products ID input by an appropriate keyboard input subroutine (step S9) is transferred to the micro-leukocytometer 17.

After the products ID for the cuvette 1 to be measured is input into the micro-leukocytometer 17, the tester initiates a measurement. For example, the tester causes the bar code reader 14 to read a predetermined bar code (the bar code indicating a command to commence measurement) (not shown). As shown in FIG. 6, the input judging portion 104 determines that the information is input (step S2) and is bar code input (step S3) and is a bar code command (step S4), whereupon the device executes the command selection subroutine (step S5).

As shown in FIG. 8, in the command selection subroutine, the input command is not found to be the registration command, but instead is the measurement command. The determination that the input is not a registration command (step S51) causes execution of a different command subroutine 1 (step S70).

Figure 9:
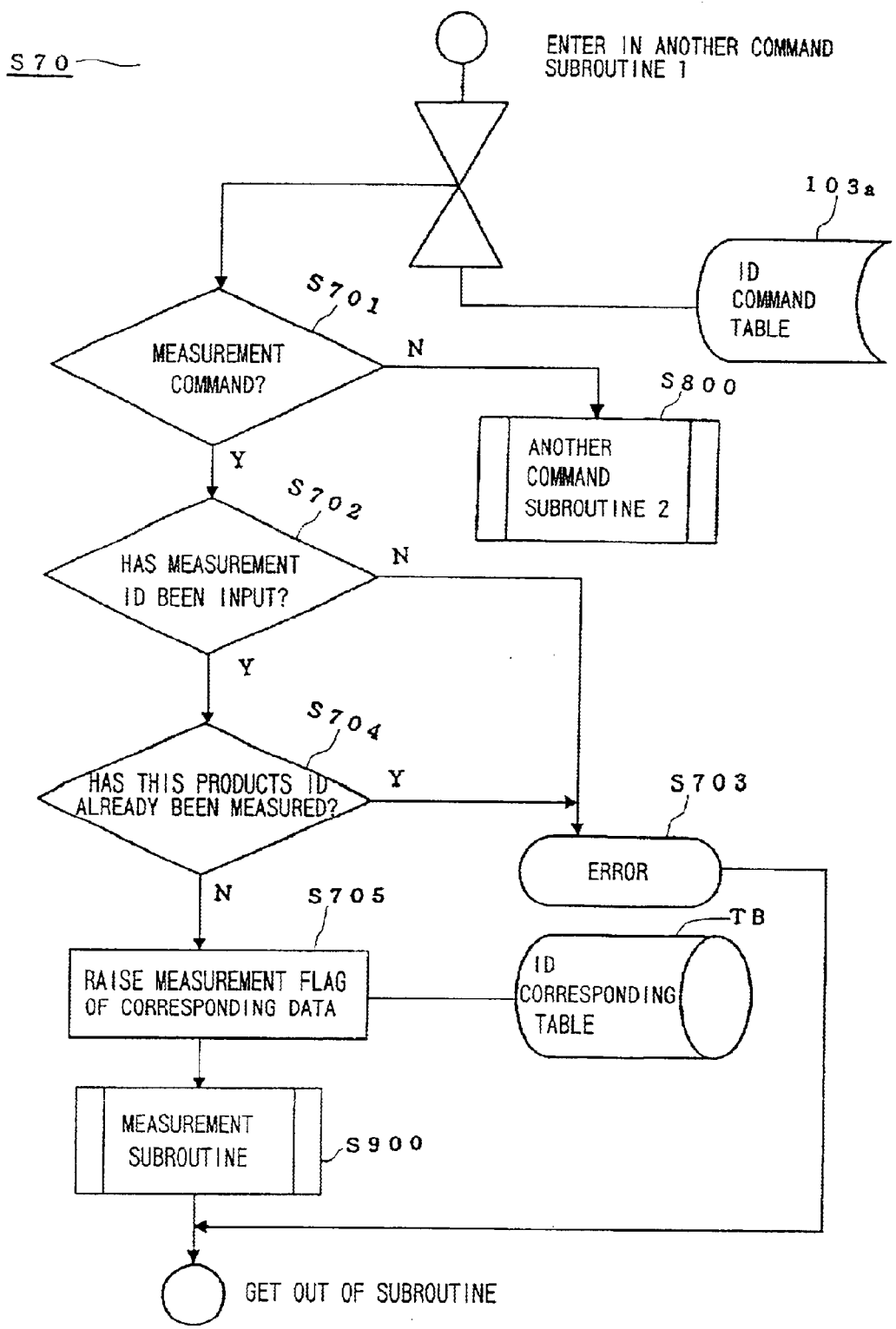
FIG. 9 is a flowchart showing another command subroutine.

FIG. 9 is a flowchart showing an example of process steps in another command subroutine 1. The bar code judging portion 106 determines that the information is a measurement command by referring to the ID command table 103a, stored in advance by the program execution portion 103 (step S701). The program proceeds with the following step S702. If the judging portion 106 determines that the information is not measurement command, the program proceeds with another command subroutine 2. In the preferred embodiment the different command leads a another subroutine (step S80) that it is not pertinent to the present invention.

When the program reaches step S702, the measurement control portion 110 communicates with the micro-leukocytometer 17, and judges whether or not a measurement ID is input. The measurement ID is comprised of the product ID input by the above-mentioned technique, and certain measurement conditions (input in the micro-leukocytometer 17 in advance). When the judgment is made that the products ID has not yet been input, the measurement step cannot proceed, and error processing is performed (step S703). The program exists the subroutine.

If the products ID has been input, the program proceeds with step S704. The measurement control portion 110 determines whether or not the products ID has been measured by referring to table TB. This judgment is made on the basis of the measurement flag provided in table TB. When the judgment is made that the products ID has been already measured in step S704, error processing is performed (step S703) since it is not necessary to execute another measurement. Theprogram exists the subroutine.

When the judgment is made that the products ID has not yet been measured in step S704, the measurement flag of the record having the corresponding products ID in table TB is set to "1" which indicates "already measured" ("not yet measured" is "0") by the measurement control portion 110 (step S705). Subsequently, the program proceeds with a predetermined measurement subroutine (step S900). In this measurement subroutine, for instance, the measurement control portion 110 allows the micro-leukocytometer 17 to measure.

The tester operates the micro-leukocytometer 17 so as to execute predetermined measurements. The measurement result is displayed and recorded on the micro-leukocytometer 17 or in the computer 15. After step S900, the program exists another command subroutine 1, and step S70 finishes, as shown in FIG. 8 control returns to step S2 from step S5, as shown in FIG. 6.

When the measurement of one cuvette 1 finishes the series of procedures is repeated for successive cuvettes in order in such a manner that the products ID is input in the micro-leukocytometer 17, and measurements are taken. By continuing, the measurement phase finishes for all of 96×n cuvettes.

According to the cuvette control unit 19 as described, various operations, such as input which has formerly been manually executed by keyboard, and correspondence between cuvette IDs and products IDs which has been manually accomplished in writing, and executed using a bar code system. Since the input in the computer 15 is executed using bar code, the input of IDs of 10 digits, for example identifying ablood collecting center where blood is collected, a place where blood is collected, a serial number and the like for the blood products ID, for instance, is made easier than possible with manually input.

The required operations are not troublesome, compared to the operation of manual entry of ID number on cuvettes with a marking ink, the operation of manual entry of corresponding cuvette IDs and blood products IDs in a notebook, etc. particularly for many cuvettes 1. The burden of such measurement operations is reduced. Mental stress and physical pain for the tester are smaller. Furthermore, input errors and repeating the same measurements two or more times, as frequently occurred in the past, can be avoided.

The tester need not carefully handle each successive cuvette 1 in order when registering and measuring. The results of registration and measurement correctly correspond without laborious checking of a notebook or the like, because the correspondence is performed by the computer 15. All that is necessary is to register the cuvette IDs in each cuvette box and the products IDs, preferably simultaneously.

The table ofbar code commands is prepared for scanning in addition to bar code ID numbers scanned as the data code input to the cuvette control unit 19. In this way, many necessary commands, such as commands to register, measure, store results, store image data, print, the setting of various values, referring to sources of help, are possible without using a keyboard or a mouse. The tester can proceed using only the bar code reader 14, without changing from one input device or even one hand to the other.

In an alternative embodiment, another bar code reader can be provided, for example with the micro-leukocytometer 17 where the cuvette 1 is placed for measurement. First, the cuvette box ID is read in. A cuvette 1 is selected and set on the measurement machine 17. The cuvette ID in the cuvette box (e.g., one of 96) is read by the bar code reader in the measurement machine 17. The cuvette and box IDs permit a search by the computer 15 for the products ID After the measurement, the product ID and measurement result are available in the computer 15, corresponding to each other. By operating thus and as mentioned before, the burden on the tester is further decreased.

Ninety six (96) of cuvettes 1, for example, are associated in a cuvette box 6. Then, ninety six (96) distinct values of the identification information INF, for instance, are necessary to distinguish the cuvettes in the box in preparation for measurement. If only forty (40) cuvettes 1, for example, were associated, the cuvettes could be identified and controlled by providing for forty distinct values of identification information INF for the cuvettes. In that case, the number of distinct cuvette identifications INF can comprise four (4) possible values of control codes and, e.g., a decimal digit providing ten (10) possible values of additional data code, resulting in forty (40) distinct values. This number of possible values is provided if either of the start code and the stop code provides four possible values (or if each has two, etc.). Forty (40) cuvettes 1 can be identified and controlled. That is, up to forty (40) cuvettes 1 can be uniquely identified and controlled if one of the two control codes (either the start code S or the stop code P) is used as a four value code carrier, without using both.

In a case where the cuvettes 1 have different size and shape permitting different numbers of digits, other numbers of cuvettes can be controlled. For example, 1600 cuvettes that are large enough for five digit bar codes can be distinguished and identified. The number of the cuvette identification information INF is 4 kinds (a–d) of start code S×100 kinds of data code I (0–99) if decimal)×4 kinds of stop code (a–d), for a total of 1600 different values, permitting 1600 cuvettes to be identified and controlled by using bar code of five digits. The present invention is explained on the basis of the heretofore, as nonlimiting examples. The embodiments which are described in the specification are illustrative. The scope of the invention is designated by the accompanying claims and is not restricted by the descriptions of the specific embodiments. Accordingly, all the transformations and changes encompassed by the claims are included in the scope of the present invention.

We claim:

1. Cuvette control unit for controlling cuvettes by reading a first bar code affixed on said cuvette, said first bar code being comprised of at least one control code located on one of two opposite end portions of said first bar code, and at least one information code located between said opposite end portions, wherein said first bar code encodes a distinct value from among a plurality of possible values, said cuvette control unit comprising:

a first reading means capable of reading said first bar code, the first reading means being operative to read said first bar code and being responsive to at least two different values of at least one said control code at one of said end portions, wherein said control code contains one of a start code and a stop code, and wherein the first reading means distinguishes among said at least two different values of said one of said start code and stop code when reading the first bar code;

a cuvette identification information producing means responsive to the first reading means, the information producing means providing a cuvette identification code based on the information code and also based on which of said different values of the at least one control code is read by the first reading means when reading said first bar code affixed to said cuvette; and a memory means for storing said cuvette identification information corresponding to said cuvette identification code.

2. The cuvette control unit as set forth in claim 1, wherein said cuvette identification information producing means provides said cuvette identification code based on at least one said control code comprising a start code at one of said end portions, in combination with said information code.

3. The cuvette control unit as set forth in claim 1, wherein said cuvette identification information producing means provides said cuvette identification code based on at least one said control code comprising a stop code at one of said end portions, in combination with said information code.

4. The cuvette control unit as set forth in claim 1, wherein said cuvette identification information producing means provides said cuvette identification codes based on two said control codes comprising both a start code at one of said end portions, a stop code at an other of said end portions, and said information code.

5. The cuvette control unit as set forth in claim 1, wherein said first bar code is comprises a start code and a stop code, on opposite ends of two digits consisting of one character of information and one character of inspection code.

6. A cuvette control unit for controlling cuvettes by reading a first bar code affixed on said cuvette and at least a second bar code affixed on a box for carrying a plurality of curettes, said first bar code being comprised of at least one control code located on one of two opposite end portions of said first bar code, and at least one information code located between said opposite end portions, wherein said first bar code encodes a distinct value from among a plurality of possible values, said cuvette control unit comprising:

a first reading means capable of reading said first bar code, the first reading means being operative to read said first bar code and being responsive to at least two different values of at least one said control code at one of said end portions, wherein said control code contains one of a start code and a stop code, and wherein the first reading means distinguishes among said at least two different values of said one of said start code and stop code when reading the first bar code;

a cuvette identification information producing means responsive to the first reading means, the information producing means providing a cuvette identification code based on the information code and also based on which of said different values of the at least one control code is read by the first reading means when reading said first bar code affixed to said cuvette;

a second reading means capable of reading said second bar code, and a cuvette box identification information producing means providing a cuvette box identification code based on the second bar code;

a memory means for storing cuvette identification information corresponding to said cuvette identification code and said box identification code; and, a storing control means for storing said cuvette identification information in the memory means, wherein said cuvette identification information is correlated in the memory to the cuvette identification code obtained from said information code combined with said at least one control code, and said cuvette box identification code.

7. A method of controlling cuvettes by reading bar codes affixed on said cuvettes, the bar codes representing digits of code, said method comprising:

respectively locating a code to be used for deleting start/stop of said bar code at both ends of said bar code affixed on each said cuvette;

selecting and using at least one code from among a plurality of start/stop codes respectively showing different values, as at least one of the codes at the ends of said bar code, used for detecting start/stop of said bar code;

identifying each said cuvette using a cuvette identification code comprising one of the different values selected for said at least one of the codes used for detecting start/stop of said bar code and also comprising a value of a code located at a portion between said ends of said bar code;

affixing to said cuvette the bar code showing the cuvette identification code; and, reading said cuvette identification code and producing cuvette identification information for controlling a plurality of the cuvettes;

wherein the cuvette identification information is determined in part from selection of the different values for at least one of said plurality of start/stop codes at the ends of said bar code.

* * * * *